(12) United States Patent
Gao et al.

(10) Patent No.: US 8,678,686 B2
(45) Date of Patent: Mar. 25, 2014

(54) MULTI-CHAIN LIPOPHILIC POLYAMINES

(75) Inventors: Xiang Gao, Pittsburgh, PA (US); Nianke Wang, Pittsburgh, PA (US)

(73) Assignee: PGR-Solutions, Pittsburgh, PA (US)

( * ) Notice: Subject to any disclaimer, the term of this patent is extended or adjusted under 35 U.S.C. 154(b) by 595 days.

(21) Appl. No.: 12/597,858

(22) PCT Filed: Apr. 30, 2008

(86) PCT No.: PCT/US2008/062080
§ 371 (c)(1),
(2), (4) Date: Mar. 29, 2010

(87) PCT Pub. No.: WO2008/137470
PCT Pub. Date: Nov. 13, 2008

(65) Prior Publication Data
US 2010/0178699 A1     Jul. 15, 2010

Related U.S. Application Data

(60) Provisional application No. 60/915,406, filed on May 1, 2007.

(51) Int. Cl.
*A61K 9/127*     (2006.01)
(52) U.S. Cl.
USPC ..................................................... 400/450
(58) Field of Classification Search
None
See application file for complete search history.

(56) References Cited

U.S. PATENT DOCUMENTS 6,171,612  B1   1/2001   Byk et al.
2004/0204377 A1 * 10/2004 Rana .............. 514/44

FOREIGN PATENT DOCUMENTS

WO     WO 98/40502 A1    9/1998
WO     WO 00/30444 A1    6/2000
WO     WO 03033027 A2 *  4/2003

OTHER PUBLICATIONS

Scanu et al, Polar and Electrooptical Properties of [60]Fullerene-Containing Poly(benzyl ether) Dendrimers in Solution, Macromolecules, 2007, 40, 1133-1139.*
Boas et al, Synthesis and Properties of New Thiourea-Functionalized Poly(propylene imine) Dendrimers and Their Role as Hosts for Urea Functionalized Guests, J. Org. Chem., 2001, 66, 2136-2145.*
Torchilin, Multifunctional nanocarriers, Advanced Drug Delivery Reviews, 2006, 58, 1532-1555.*
Behr et al., Jean-Paul, "Efficient gene transfer into mammalian primary endocrine cells with lipopolyamine-coated DNA", Proc. Natl. Acad. Sci. USA, vol. 86, pp. 6982-6986, Sep. 1989.
Boussif et al., Otmane, "A versatile vector for gene and oligonucleotide transfer into cells in culture and in vivo: Polyethylenimine", Proc. Natl. Acad. Sci. USA, vol. 92, pp. 7297-7301, Aug. 1995.
Chen, et al., Chris Zhisheng, "Quaternary Ammonium Functionalized Poly(propylene imine) Dendrimers as Effective Antimicrobials: Structure-Activity Studies", Biomacromolecules 2000, 1, pp. 473-480.
Kramer et al., Michael, "pH-Responsive Molecular Nanocarriers Based on Dendritic Core-Shell Architectures", Angew. Chem. Int. Ed. 41, No. 22, pp. 4252-4256, 2002.

(Continued)

*Primary Examiner* — Paul Dickinson
(74) *Attorney, Agent, or Firm* — The Marbury Law Group, PLLC

(57) ABSTRACT

There are provided multi-chain lipophilic polyamine compounds and derivatives thereof, pharmaceutical formulations comprising the same, method of making and using said compounds or formulations.

12 Claims, 10 Drawing Sheets

Example Structures of polyamines

(56) References Cited

OTHER PUBLICATIONS

Mizutani, Hirotsugu, "Physicochemical Properties of Quaternized Poly(amidoamine) Dendrimers with Alkyl Groups and of Their Mixtures with Sodium Dodecyl Sulfate", Journal of Colloid and Interface Science, 248, pp. 493-498, 2002.

Murugan et al., Eagambaram, "Catalysis by Hydrophobically Modified Poly(propylenimine) Dendrimers Having Quaternary Ammonium and Tertiary Amine Functionality", Langmuir, 20, pp. 8307-8312, 2004.

Schenning et al., Albertus P.H.J., "Amphiphilic Dendrimers as Building Blocks in Supramolecular Assemblies", J. Am. Chem. Soc., 120, pp. 8199-8208, 1998.

Sui et al., Guodong, "A Structural Study of Amphiphilic PAMAM (Poly(amido amine)) Dendrimers in Langmuir and Langmuir-Blodgett Films", Journal of Colloid and Interface Science, 250, pp. 364-370, 2002.

Yamazaki et al., Y., "Polycation liposomes, a novel nonviral gene transfer system, constructed from cetylated polyethylenimine", Gene Therapy, 7, pp. 1148-1155, 2000.

PCT/US/2008/062080, filed Apr. 30, 2008, Intl. Search Report dated Aug. 26, 2008 (2 pages).

* cited by examiner

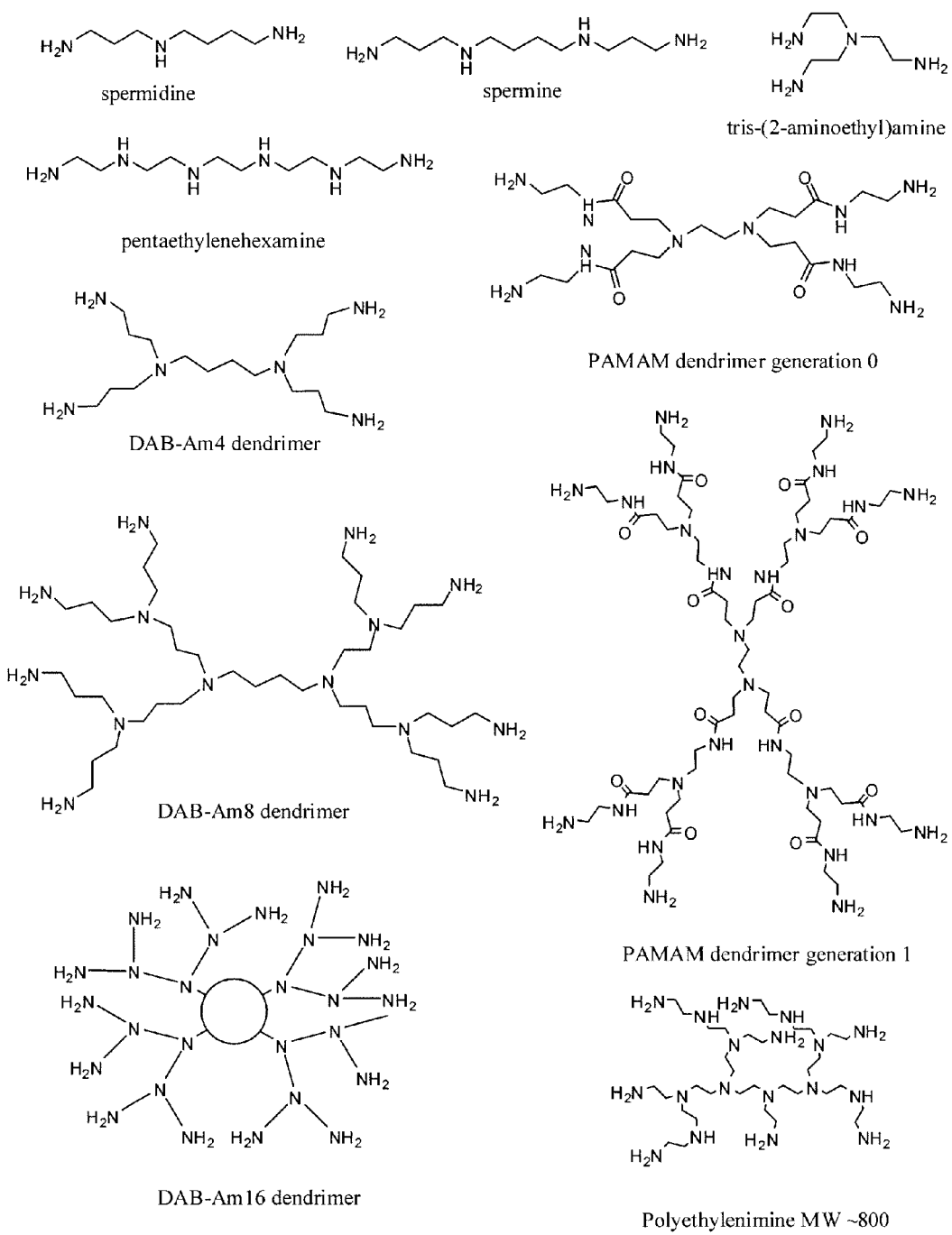
Figure 1 Example Structures of polyamines

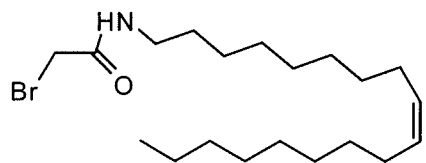
1) 2-bromoacetamido-olean
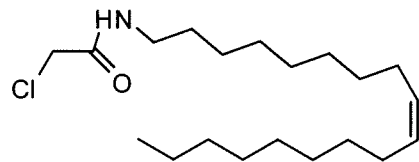
2) 2-chloroacetamido-olean
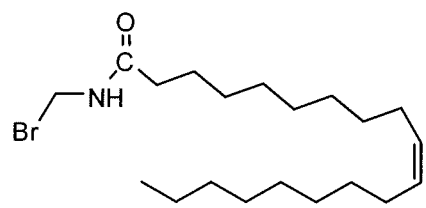
3) N-Oleoyl-2-bromoethylamide
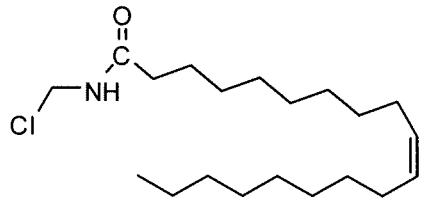
4) N-Oleoyl-2-chloroethylamide
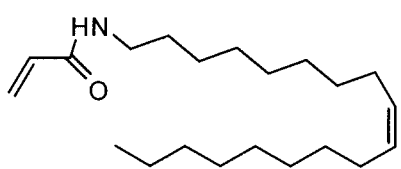
5) 2-acryloylamido-olean
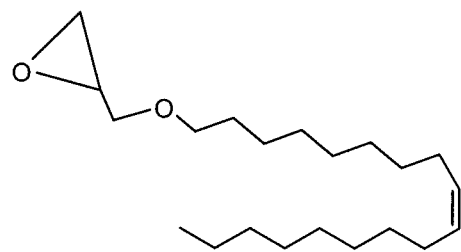
6) Oleyl glycidyl ether
Figure 2 Example Structures of Lipid Derivatives

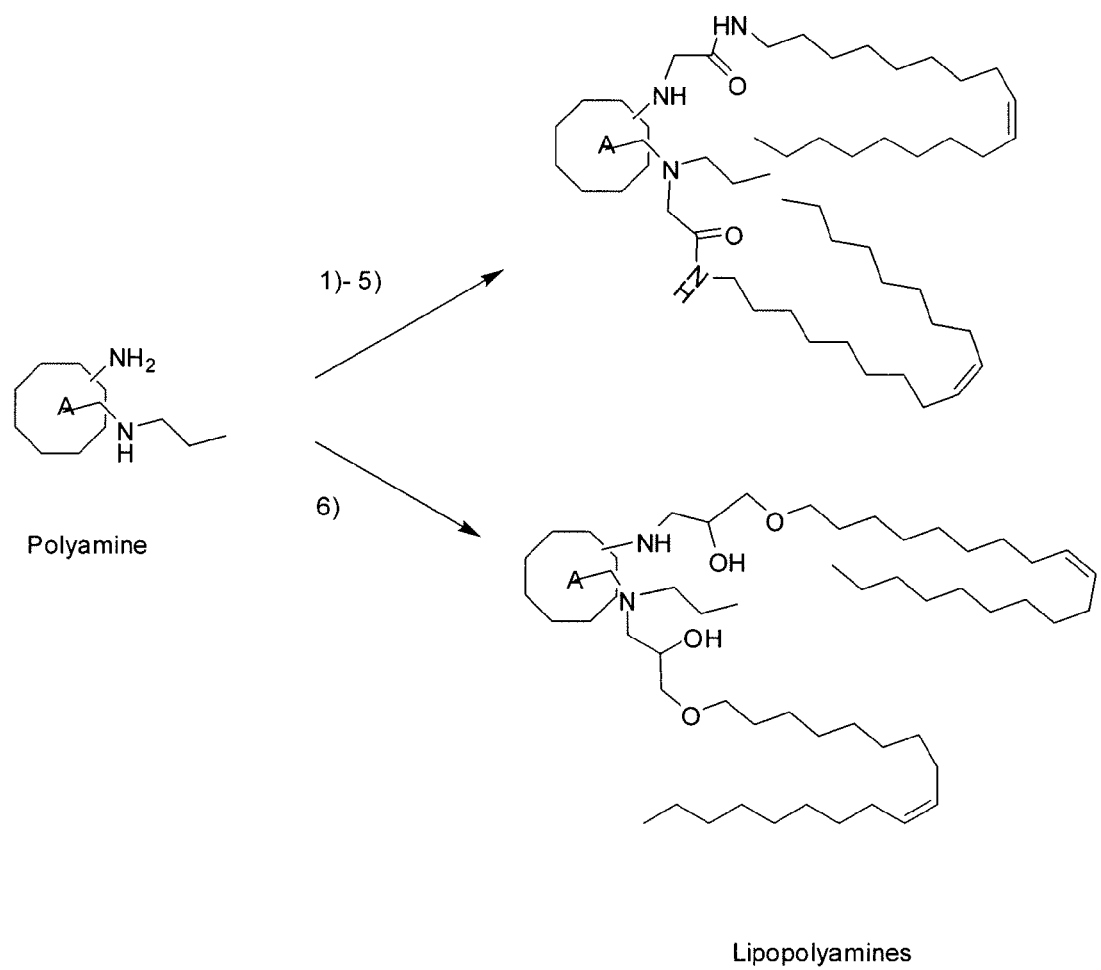
Figure 3 Example Synthesis Scheme of lipopolyamines

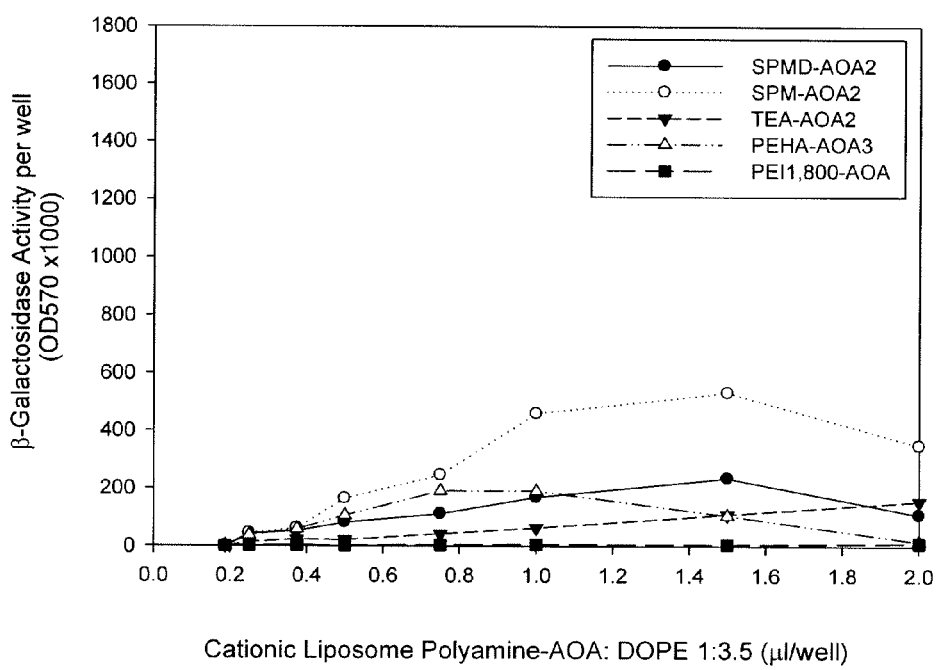

Figure 4 a Transfection activities of cationic liposomes with lipopolyamines synthesized from spermidine (SPMD), sperimine (SPM), tris-(2-aminoethyl)amine (TEA), pentaethylenehexamine (PEHA) and branched polyethylenimine with a molecular weight of 1,800 (PEI1,800) and bromoacetamide derivative of oleylamine (AOA). The CV-1 cells (15,000 cells) in 96 well plates were transfected with complexes formed using 0.3 μg pCMVβGal DNA/well and the indicated amounts of liposomes. The liposomes were composed of 200 nmoles lipopolyamines and 700 nmoles of DOPE per ml. β-Galactosidase activity was measure with CRPG substrate at 36 hr post transfection.

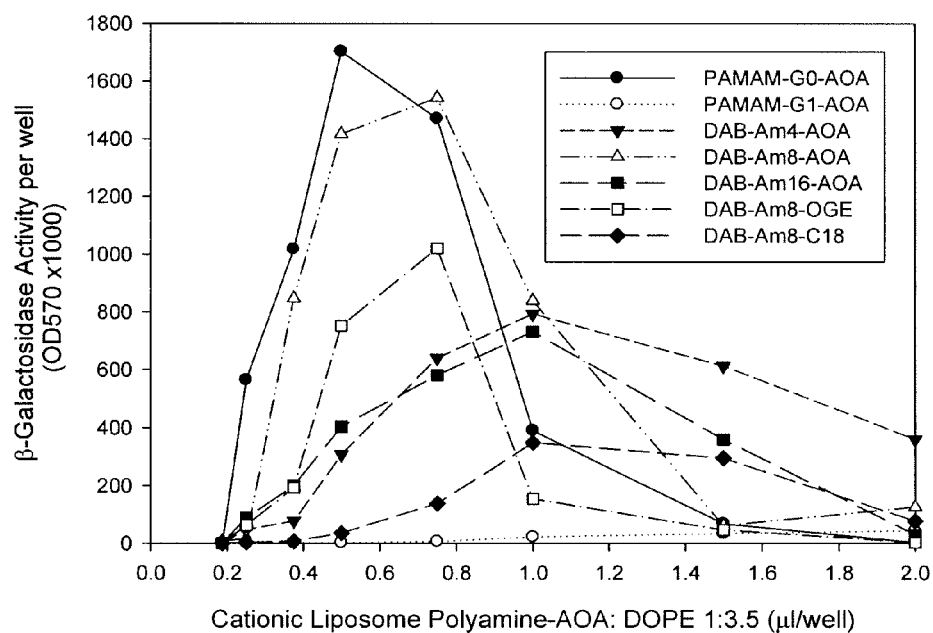

Figure 4 b Transfection activities of cationic liposomes with lipopolyamines synthesized from polyamindoamine dendrimer generation 0 (PAMAM G0), generation 1 (PAMAM G1), polypropylimine dendrimer G1 (DAB-Am-4), G2 (DAB-Am-8), G3 (DAB-Am-16) with bromoacetamide derivative of oleylamine (AOA), and analogues of DAB-Am8 reacted with oleyl glycidyl ether (OGE) or bromo C18 (C18). The CV-1 cells (15,000 cells) in 96 well plates were transfected with complexes formed using 0.3 μg pCMVβGal DNA/well and the indicated amounts of liposomes. The liposomes were composed of 200 nmoles lipopolyamines and 700 nmoles of DOPE per ml. β-Galactosidase activity was measure with CRPG substrate at 36 hr post transfection.

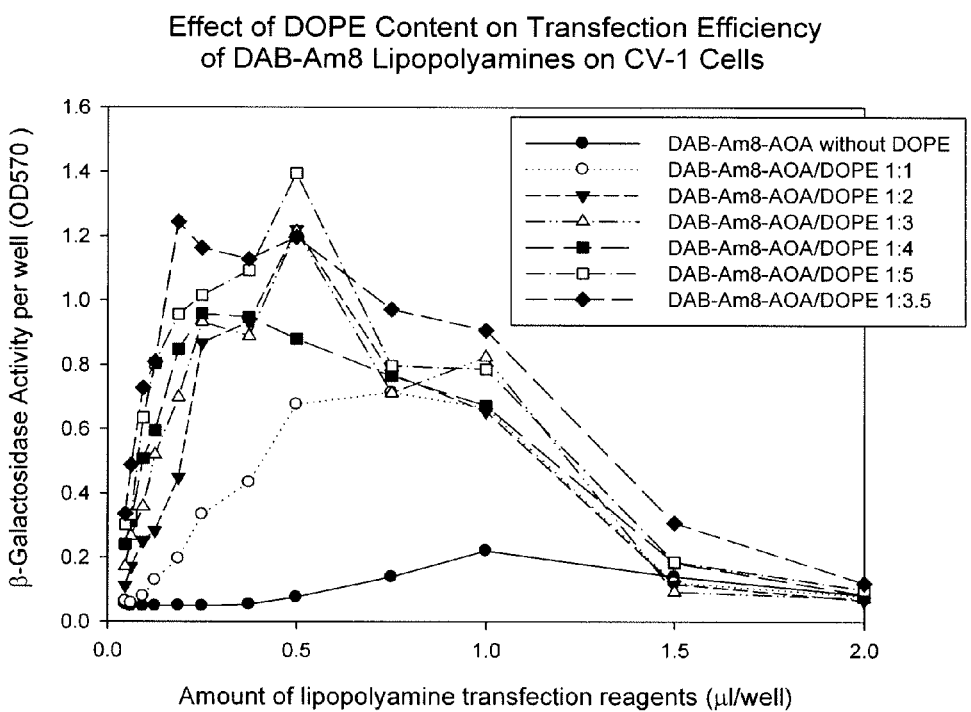
Figure 5 a. The effect of DOPE content on transfection activity of cationic liposomes prepared from lipo-DAB-Am8-AOA6. The liposomes were prepared from 200 nmoles of DAB-AOA and indicated amounts of DOPE ranging from none, 1:1 to 1:5 mole ratios in 1 ml distilled water. The amount of DNA used was 0.3 µg per well. Cells were harvested at 24 hrs post transfection.

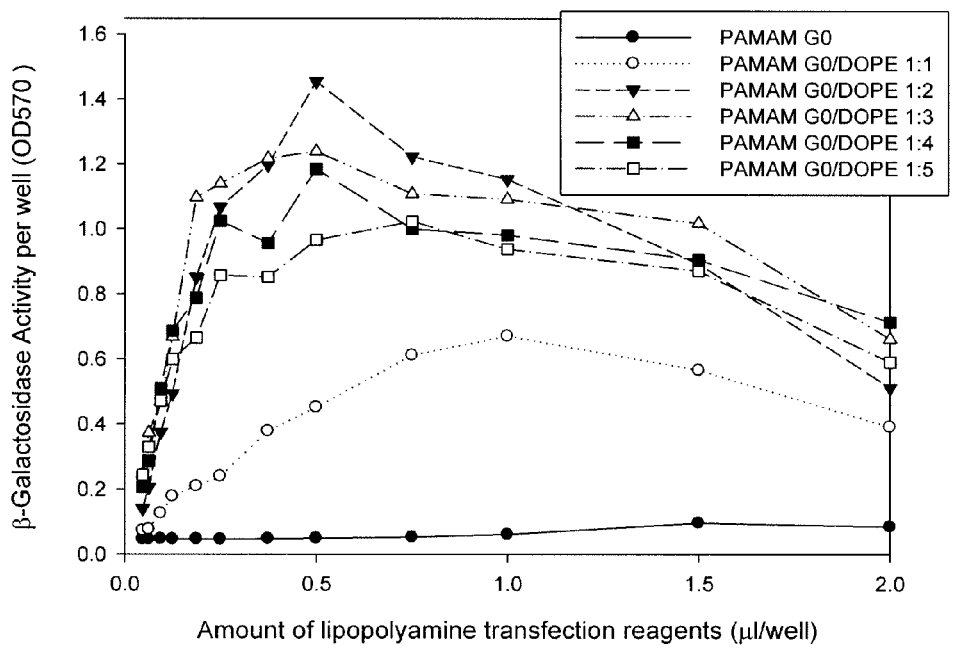
Figure 5 b. The effect of DOPE content on transfection activity of cationic liposomes prepared from lipo-PMAMA-G0. The liposomes were prepared from 200 nmoles of lipo-PAMAM-G0 and indicated amounts of DOPE ranging from none, 1:1 to 1:5 mole ratios in 1 ml distilled water. The amount of DNA used was 0.3 µg per well. Cells were harvested at 24 hrs post transfection.

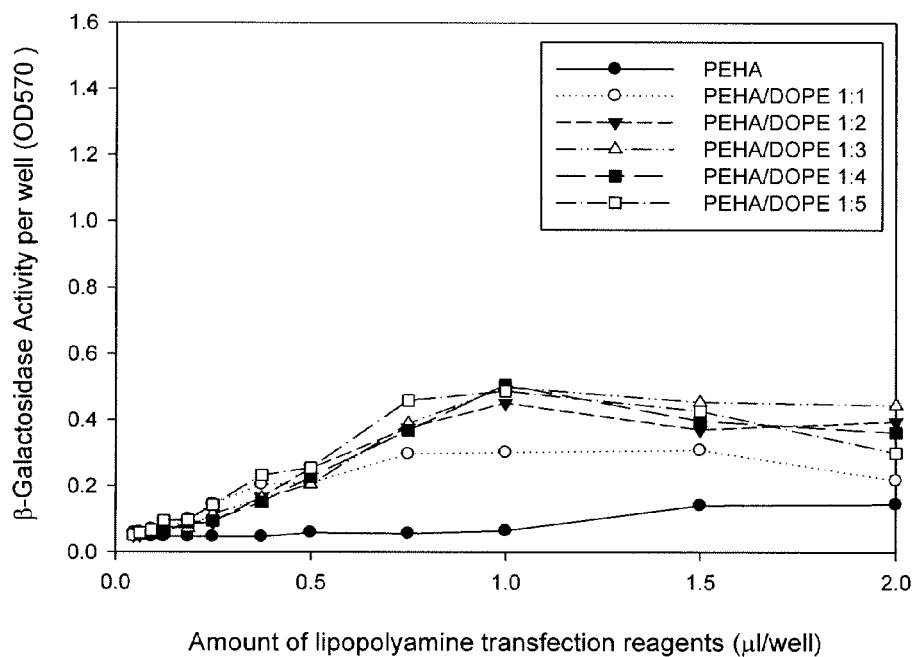
Figure 5 c. The effect of DOPE content on transfection activity of cationic liposomes prepared from lipo-pentaethylenehexamine (PEHA-AOA3). The liposomes were prepared from 200 nmoles of lipo-PEHA and indicated amounts of DOPE ranging from none, 1:1 to 1:5 mole ratios in 1 ml distilled water. The amount of DNA used was 0.3 µg per well. Cells were harvested at 24 hrs post transfection.

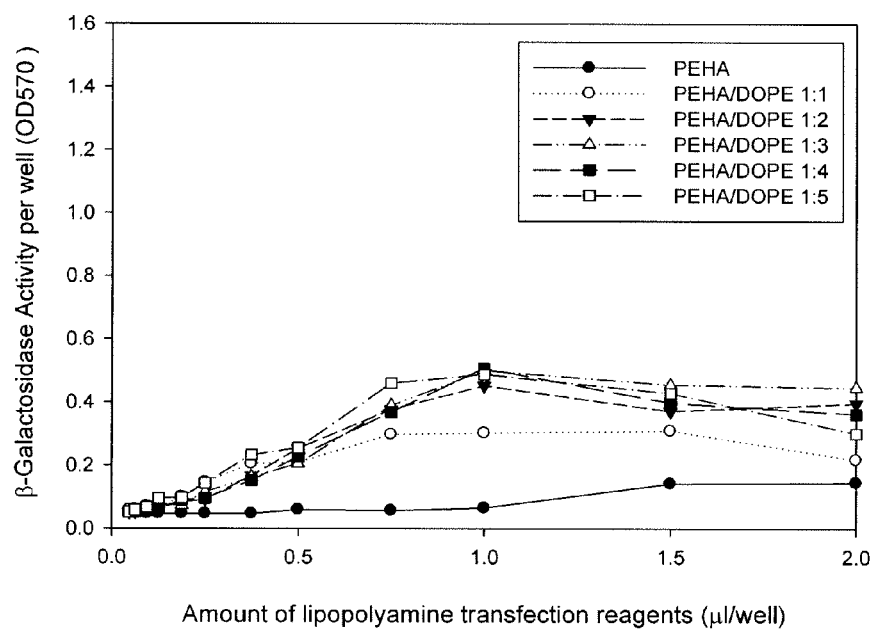
Figure 6 Transfection efficiency of lipo-DAB-Am8-AOA6:DOPE liposomes with varied dosages of DNA. The transfected cells were harvested at 24 hrs post transfection.

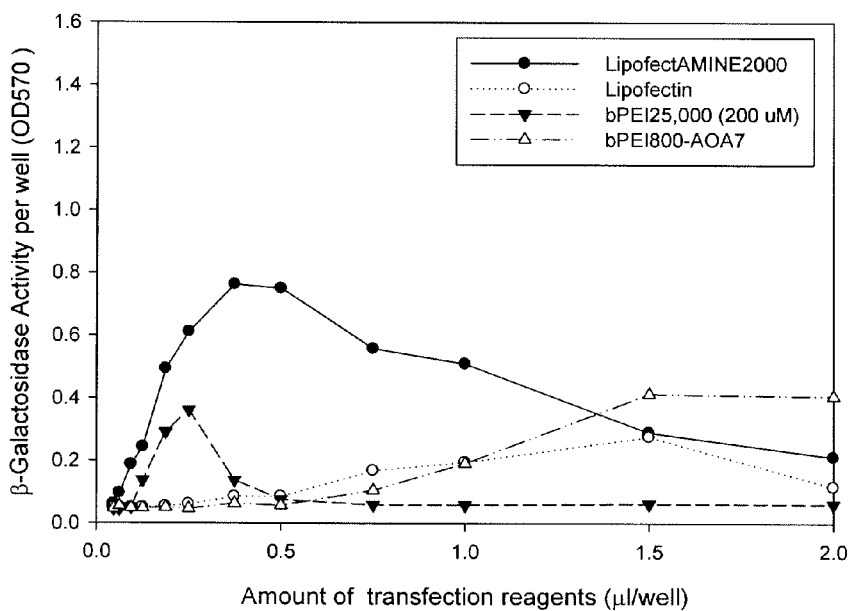

Figure 7 Transfections mediated by LipofectAMINE®, Lipofectin®, branched PEI25,000, a cationic liposomes formulation with lipopolyamine prepared from branched PEI800 and AOA co-formulated with DOPE was also included. Figure 6,7 and 8 were from data collected in a single experiment. The relative transfection activities for different formulations were therefore comparable.

MULTI-CHAIN LIPOPHILIC POLYAMINES

This application is a U.S. National Stage entry for PCT application serial no. PCT/US2008/062080 filed Apr. 30, 2008, which is hereby incorporated by reference in its entirety and which claims priority to U.S. Provisional application 60/915,406 filed May 1, 2007, which is also incorporated by reference in its entirety.

BACKGROUND

A need exists to provide better materials for incorporating materials into cells including better transfection agents. For example, many transfection agents suffer from toxicity problems, or low transfection efficiency, or sensitivity to serum.

SUMMARY

Described herein are compounds, compositions, methods of making, and methods of using.

This invention relates generally to a class of lipophilic polyamine compounds prepared from linear, branched and dendritic polyamines and long chain lipid derivatives with a nucleophilic reacting group through direct alkylation, ring-opening substitution, or Michael addition on the amine groups. The reaction converted the primary and secondary amine groups on the polyamines to secondary or tertiary amines, correspondingly. The lipopolyamine derivatives can be a collection of mixed isomers with multiple lipid groups randomly linked to the polyamine. When suspended in water, the lipopolyamines form micelle. Liposomes are formed when suspension is made from a mixture of lipopolyamines with diacyl phosphotidyl choline; diacyl phosphotidyl ethanolamine, or with diacyl phosphotidyl choline or ethanolamine together with cholesterol of different proportion. Varied levels of cell transfection activities are noticed in lipopolyamines reported here, while the lipopolyamines prepared from low generations of dendrimers are among the most potent cell transfection activity tested from this class of polymer derivatives.

One embodiment provides a lipopolyamine comprising:

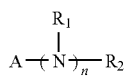

Formula I wherein $A\text{-}(\!\text{-}N)_n$ is linear, branched or dendritic polyamine, wherein n=3-100;

$R_1$ is independently H, or a substitute of structure (X—Y—Z) wherein
  X=$(CH_2)_i$, wherein i=0-12 and when i=0, X is a bond, —$(CH_2)_iC(O)$—, —$(CH_2)_iNH$— wherein i=0-12, or —$CH_2CH(OH)CH_2$—,
  Y=a bond, —C(O)NH—, —NHC(O)—, —$CH_2$—, —O—, —C(O)O—, or —C(O)—;
  Z=linear or branched alkyl or alkenyl chain having 4-40 carbon units;

$R_2$ is a substitute of structure of $(X\text{—}Y\text{—}Z)_m$, wherein
  X=$(CH_2)_i$, wherein i=0-12 and when i=0, X is a bond, —$(CH_2)_iC(O)$—, —$(CH_2)_iNH$— wherein i=0-12, or —$CH_2CH(OH)CH_2$—;
  Y=a bond, —C(O)NH—, —NHC(O)—, —$CH_2$—, —O—, —C(O)O—, or —C(O)—;
  Z=linear or branched alkyl or alkenyl chain having 4-40 carbon units;
  m is at least 1 or any integer between 1 to 2n;

in pure form or in mixture of isomers, or in form of any lipid polymorphism phase known to exist, or its solvates, hydrates, isomers, and any salts, for example pharmaceutically acceptable salts.

BRIEF DESCRIPTION OF THE DRAWINGS

FIG. 1 shows some examples of the structures of polyamines used for the construction of lipopolyamines.

FIG. 2 shows some examples of the structures of lipid intermediates that carry a reactive group.

FIG. 3 shows examples of synthetic scheme for the lipopolymers using different lipid intermediates.

FIGS. 4a and b show the transfection efficiency of lipopolyamines-DOPE liposomes.

FIGS. 5a-c show the importance of the co-lipid DOPE in transfection efficiency of three most active lipopolyamines.

FIG. 6 shows that the optimal DNA dosages for an efficient transfection using lipopolyamine DAB-Am8-AOA6:DOPE (1:3.5) requires a minimal of 0.2 µg/well for 96 well plates, while the optimal dosages appeared to be ≥0.3 µg/well.

FIG. 7 shows the transfection efficiency of several well known and widely used commercial transfection reagents.

DETAILED DESCRIPTION

Introduction

Transfection is a process by which nucleic acid molecules are introduced into cells by physical or chemical means. Transfection is a routine technique used to study the function and the regulation of gene and gene delivery is also the basis for emerging nucleic acid-based therapeutic applications. Chemical gene transfer method requires the uses of an agent of polymer or lipid of nature that carries positive charges. Such agents are also called carriers, which form complexes with negatively charged DNA or RNA molecules through static charge-charge interactions. These complexes are particles of 20 nm to several µm in sizes and have positive surface charges. The nucleic acid molecules in these particles are well protected from enzymatic degradation; these particles also facilitate the cellular uptake and subsequent intracellular release of the nucleic acids. Although this technique is routinely used for transfection on cells grown in tissue culture, it has been used to introduce genes, antisense oligonucleotides or siRNA into cells in animals or humans for functional genetic research or therapeutic purposes.

Cationic lipids, alone or mixed with non-cationic lipids or steroids, form micelle, liposomes, emulsion, or other types of lipid aggregates in aqueous solution. Cationic lipids interact with anionic nucleic acids through static charge-charge attractions, resulted in condensed nanoparticles carrying overall cationic charges. These nanoparticles in turn interact with eukaryotic cells and trigger efficiency uptake of cationic lipid-DNA complexes that ultimately lead to the intracellular delivery of the nucleic acid. Such agents have been widely used as an essential research tool to introduce a piece of DNA that codes for specific genetic information that can be translated into a particular polypeptide sequence into a cell to study the effect of a gain-of-function on cellular activity and metabolism. Recently, small single stranded antisense oligonulceotides or double stranded small interference RNAs have been developed to interrupt the cellular expression of a particular gene to study the effect of a lost-of-function on cellular activity and metabolism. It also has been used for the production of recombinant proteins as well as recombinant virus in large scale cell culture through transient transfection. New therapies based on in vivo delivery of genes, antisense oligonucleotides, or siRNAs of therapeutic potential have been demonstrated in animals and human clinical trials using this method. To maximize the potential application of this method, cationic lipids with reduced cytotoxicity and improved transfection activity are in great demand.

Here, we disclose several lipopolymers made by conjugation lipids to a polyamine with or without a spacer, that these lipopolyamines when co-formulated with DOPE, can interact with DNA to form DNA-liposome complexes that are capable of mediating efficient transfection at dosages that does not cause significant toxicity and does so in the presence of serum in cell culture, therefore without the need to replace the transfection reagent throughout the process. These formulations appear to mediate transfection without the need of excessive liposomes like most existing reagents do. We have shown that the liposomes prepared from the diacyl phosphotidyl ethanolamine and lipophilic dendrimers showed equal or better transfection activities when compared to several commercially available transfection reagents. These formulations provide a simplified and efficient transfection at dosages that cause minimal cytotoxicity.

Here lipopolyamine is used interchangeably with lipophilic polyamine, biologically active agent is used interchangeably with bioactive agent.

Compounds

One object of this invention is a lipopolyamine having structure of Formula I:

Formula I wherein

A—(N)$_n$ is linear, branched or dendritic polyamine, wherein n=3-100;

R$_1$ is independently H or a substitute of structure (X—Y—Z) wherein

X=(CH$_2$)$_i$, wherein i=0-12 and when i=0, X is a bond, —(CH$_2$)$_i$C(O)—, —(CH$_2$)$_i$NH— wherein i=0-12, or —CH$_2$CH(OH)CH$_2$—, Y=a bond, —C(O)NH—, —NHC(O)—, —CH$_2$—, —O—, —C(O)O—, or —C(O)—;

Z=linear or branched alkyl or alkenyl chain having 4-40 carbon units

R2 is a substitute of structure of (X—Y—Z)$_m$, wherein

X=—(CH$_2$)$_i$— wherein i=0-12 and when i=0, X is a bond, or —(CH$_2$)$_i$C(O)—, —(CH$_2$)$_i$NH— wherein i=0-12, or —CH$_2$CH(OH)CH$_2$—;

Y=a bond, —C(O)NH—, —NHC(O)—, —CH$_2$—, —O—, —C(O)O—, or —C(O)—;

Z=linear or branched alkyl or alkenyl chain having 4-40 carbon units m is at least 1 or any integer between 1 to 2n;

in pure form or in mixture of isomers, or in form of any lipid polymorphism phase known to exist, or its solvates, hydrates, isomers, and any salts, for example pharmaceutically acceptable salts.

This present invention relates to a polyamine derivative represented by general formula I, wherein A-(N)$_n$— is a polyamine with n amino groups (n=3-100). It is a linear polyamine, a branched polyamine or a polymer with dendritic shape in architecture. R$_1$ is a H, or a substitute group of structure of (X—Y—Z); R$_1$ group can be a long chain lipid group derived from fatty amine, alcohol, or acid with homogenous chain length or a mixture of more than one types of long chain fatty amine, alcohol, or acid with heterogeneous chain length. Z is individually a linear or branched alkyl or alkenyl group, identical to or different from each other, which may have at least 4-40 carbon atoms in length, each Z group is linked to the amine groups of the said polyamine through a spacer X. Spacer X is —(CH2)$_i$—, —(CH$_2$)$_i$C(O)— or —(CH$_2$)$_i$—NH— wherein i=0-12 or —CH$_2$CH(OH)CH$_2$—. Each X may have 0-12 carbon atoms in length, linear or branched, with or without at least one hydroxyl substitute group. X is linked to the Z group through a chemical bond Y, Y can be a bond, —C(O)NH—, NHC(O)—, —C(O)O—, or —O—. The lipid is conjugated to the said polyamine through a lipid intermediate bearing a reactive terminal group, such as a halide group, an acryloyl group, a glycidyl group, an aldehyde or an keto group, such that each conjugation of the lipid derivative result in an increase in the order of the substituted amine on the said polyamine. The conjugation of the lipid derivative to the said polyamine occurs in a random manner which leads to a mixture of isomers with varied number of lipids (m) linked to a single polymer and the number m is at least 1 or any integer in the range of 1 to 2n.

The lipopolyamine in this invention can be in the form of free base or in the form of a salt of one or more inorganic or organic acids. The examples of such inorganic or organic acid are hydrogen bromide or chloride, acetic acid, sulfuric acid, nitric acid, methyl sulfate, trifluoroacetic acid, tosulate, oxalate, valarate, oleate, laurate, borate, benzoate, lactate, phosphate, carbonate, citrate, maleate, fumarate, succinate, tartrate, and the like.

A partially or fully protonated polyamine derivative with any inorganic or organic acid carries cationic charges. Said derivative alone forms micelle when suspended in neutral or acidic aqueous solution; it forms liposomes when mixed with other lipids, such as cholesterol and phosphatidyl ethanolamine or phosphatidyl choline when suspended in neutral or acidic aqueous solution. Both lipid aggregation forms are capable of forming complexes with nucleic acid or polypeptides that carry anionic charges and have the utility to deliver these macromolecules into the cytosol inside cells.

Method of Making

One object of this invention is a method of making said lipopolyamine in its pure form or in mixture of isomers, its solvate, hydrate, isomer or pharmaceutically acceptable salts. Said method comprises a covalently coupling of a polyamine and a reactive lipid intermediate wherein the amino group(s) in said polyamine reacts with a halide, epoxy, acryloyl, and acid, acid chloride, aldehyde or keto group of said lipid intermediate or lipid itself, such as a fatty acid. The halogen is selected from F, Cl, Br, and I. FIG. 3 shows some examples of lipopolyamine synthesis using reactive lipid intermediates. It should be understood that the method of this invention is not limited to said examples.

Examples of the lipids related to this invention are laurylamine, myristylamine, palmitylamine, oleylamine, stearylamine, oleyl alcohol, oleic acid. Oleyl chain contains a single double bond, which provided flexibility to the lipid molecule and lowed melting temperature. Other mono- or poly-unsaturated lipids with different chain length may also be used for such purpose. Saturated or solid chain of C4 to C40 in length may also be used for the preparation of the active intermediates. It should be understood that the method of this invention is not limited to said examples.

Three categories of reacting groups (halo, epoxy, and acryloyl) can be introduced to the readily available long chain lipids. Haloacetamido-lipid intermediates are formed by reacting fatty amines with chloroacetic or bromoacetic chloride or bromide; haloethylamide-lipid intermediates are formed by reacting fatty acids with 2-bromo or 2-chloro ethyl amine; acryloyl amido-lipid intermediates are formed by reacting fatty amines with acryloyl chloride or bromide; lipid-glycidyl ethers are formed by reacting fatty alcohols with epichlorohydrin. Examples of the reactive lipid intermediates include but not limited to 2-bromoacetamido-olean, 2-chloroacetamido-olean, N-oleoyl-2-bromoethylamide, N-oleoyl-2-chloroethylamide, 2-acryloylamido olean, oleyl glycidyl ether, and (Z)-nonadec-10-enoyl chloride. Some lipids, such as fatty acids, are reactive without forming a reactive intermediate.

The polyamines in this invention include but not limited to spermidine (SPMD), spermine (SPM), tris-(2-aminoethyl)amine (TEA), pentaethylenehexamine (PEHA), linear polyethylenimine (LPEI), PAMAM dendrimer G0, PAMAM dendrimer G1, DAB-Am4 dendrimer, DAB-Am8 dendrimer, DAB-Am16 dendrimer, or branched polyethylenimine MW ~800.

In one embodiment, the polyamine reacts with the acryloyl group of a lipid intermediate through a Michael addition reaction. In one embodiment, the polyamine reacts with the epoxy group of the lipid intermediate through a ring opening substitution reaction. In one embodiment, the polyamine reacts with the halide group of the lipid intermediate through a substitution reaction.

WORKING EXAMPLES

The syntheses of some of the reactive lipid intermediates are shown further in the following non-limiting working examples:

Example 1

Haloacetamido-alkane or alkenes: Oleylamine, palmitylamine, stearylamine was reacted with chloroacetic chloride or bromide or bromoacetic chloride or bromide in the presence of a triethylamine (TEA) base in $CH_2Cl_2$. After routine work up, the resulted N-haloacetamido-alkane or alkenes were purified by chromatograph on silica gel (Hexane:ethyl acetate 15:85).

Example 2

Acryloylamido alkane or alkenes: Oleylamine was treated with acryloyl chloride in the presence of TEA in $CH_2Cl_2$. After routine work up, the resulted acryloylamido-olean was purified by chromatograph on silica gel (Hexane:ethyl acetate 10:90).

Example 3

1,2-epoxy-3-cis-9-octadecenoxypropane (or oleyl glycidyl ether): Oleyl alcohol in DMSO was treated with crushed KOH pellet and two molar excess of epichlorohydrin at 60° C. for 48 hrs. After routine work up, the resulted epoxypropy oleyl ether was purified by chromatograph on silica gel (Hexane:ethyl acetate 10:90).

Example 4

Other lipid derivatives with a nucleophilic reacting group could also be readily prepared including: reacting iodoacetic chloride, chloroethyl chloroformate, or 2-chloroethyl isothiocyanate with an alkyl or alkenyl amine;

Example 5

Alternatively, 2-chloroethylamine or 2-bromoethylamine reacts with a long chain fatty acid, such as oleic acid, either with the activated acyl chloride or by a dehydrating agent. Commercially available alkyl iodine, bromide, or chloride can also been used.

The synthesis of said lipopolyamine is illustrated but not limited to the following examples:

Example 6

Synthesis of Lipophilic Polyamines Using Haloacetamido Olean

Polyamine (0.1 mmole) in ethanol was added with haloacetamido alkane or alkene at varied molar ratio of amino nitrogen to alkylating lipid derivative, followed by 1 equivalent of $Na_2CO_3$ to alkylating agents dissolved in small amount of water. The solutions were heated to 70° C. The progress was monitored by TLC test and was completed at the end of 24-48 hrs based on the total consumption of the alkylating agents. The resulted polyamine derivatives are obviously a mixture of analogous with different numbers of lipid chains linked to the polyamine. After evaporation of the solvent, the resulted lipidic polyamines were dissolved in methanol-$CHCl_3$ (1:1 vol/vol) at a concentration of 20 mM according to the original polyamine and stored at −20° C.

Example 7

Synthesis of Lipophilic Polyamines Using Oleyl Glycidyl Ether

Polyamine (0.1 mmole) in ethanol was added with oleyl glycidyl ether at varied molar ratio of amino nitrogen to alkylating lipid derivative. The solutions were heated to 70° C. The progress was monitored by TLC test and was completed at the end of 48 hrs based on the total consumption of the alkylating agents. The resulted polyamine derivatives are obviously a mixture of analogous with different numbers of lipid chains linked to the polyamine. After evaporation of the solvent, the resulted lipidic polyamines were dissolved in methanol-$CHCl_3$ (1:1 vol/vol) at a concentration of 20 mM according to the original polyamine and stored at −20° C.

Example 8

Synthesis of Lipophilic Polyamines Using Acryloylamido-olean

Polyamine (0.1 mmole) in ethanol was added with acryloylamido-olean at varied molar ratio of amino nitrogen to alkylating lipid derivative. The solutions were heated to 70° C. The progress was monitored by TLC test and was completed at the end of 48 hrs based on the total consumption of the alkylating agents. The resulted polyamine derivatives are obviously a mixture of analogous with different numbers of lipid chains linked to the polyamine. After evaporation of the solvent, the resulted lipidic polyamines were dissolved in methanol-$CHCl_3$ (1:1 vol/vol) at a concentration of 20 mM according to the original polyamine and stored at −20° C.

In terms of reactivity, the haloacetamido compounds are more reactive than epoxy or acryloylamido lipid derivative, as the later two require considerable longer reaction time to reach completion at the same reaction temperature than the haloacetamido compounds. Both bromo and chloride derivative are reactive enough under the condition. The bromo compound yielded darker color than the chloro compound, both as lipid intermediates or after reaction to produce lipopolyamines.

As any person with the knowledge in the field should know, the reaction by alkylation at elevated temperature is expected to be random modification and the end products should be a mixture of lipopolymers with varied numbers of lipid chains conjugated to the amino groups. Some $NH_2$ may be unmodified; while others may be conjugated with two or three lipid chains. However, it is expected that under the condition that was used, the majority of the lipopolymer should contain a total number of the lipid chains close to the initial ratio of amine to lipid intermediate. As it is difficult to purify individual species of the lipopolycations, the end product was used as is, without purification. However, using known purification methods, such as phase partition, vacuum distillation, size exclusion, ionic exchange or hydrophobic interaction chromatography, or electrophoresis methods, either used individually, or in combination, individual or group of the modified lipopolyamines can be fractionated or purified from the mixture. It is expected that purified or fractionated lipopolyamines with more defined chemical structures may behave differently from the mixtures and further improvement of the transfection activity can be expected from the purified lipopolyamines as compared to unpurified mixture.

Compositions

One objection of this invention is a micelle or liposome composition comprising a lipid agent. Said lipid agent comprises a lipopolyamine in its pure form or in mixture of isomers or its solvates, hydrates, isomers or any salts, for example pharmaceutically acceptable salts, one or more biologically active agents (or bioactive agents), one or more second lipids ("helper" lipids) and one or more pharmaceutically acceptable solvents, carriers, or additives.

The bioactive agent in the composition can be a polynucleotide, a polypeptide, a polypeptide with carbohydrate groups on its side chains, a polysaccharide or a chemical such as a small molecule drug.

The polynucleotide can be DNA or mRNA coding for a polypeptide which is expressed after the DNA or mRNA is taken up into a cell. Said polynucleotide can also be an oligonucleotide in single stranded form or in fully or partially complementary double stranded form. Said polynucleotide can also be a RNA. Said nucleotide may have diester linkages or other chemically modified linkages. The bioactive agent can be a polypeptide or a polypeptide derivative. The bioactive agent can be a chemical compound, such as a drug. Many drugs are hydrophilic and do not readily cross cellular membrane. The formulation of this invention helps such drugs cross cellular membrane and hence improves bioavailability.

The lipid agent in this invention comprises a lipopolyamine in its pure form or as a mixture of the lipopolyamine and one or more types of "helper" lipids. The helper lipids, also called co-lipids are not active in transaction by themselves. However, the inclusion of these helper-lipids can substantially alter the biological activities of the lipopolyamines. Helper lipids are of different chemical structure from the lipopolyamine. They can be of neutral, anionic or cationic charge. Some examples of the helper lipids are but not limited to cholestraol or its derivatives, monoacyl or diacyl phosphatidyl choline, monoacyl or diacyl phosphatidyl ethanolaime, mono and dimethyl derivative of a monoacyl or diacyl phosphatidyl ethanolamine, monoacyl or diacyl phosphatidyl serine, a single chain fatty alcohol, fatty acid or fatty amine.

The lipid agent can be in form of any type of lipid polymorphism phase known to exist.

In the formulation of this invention, the bioactive agent is absorbed to the lipid molecule or entrapped within the lipid vesicles.

The composition/formulation can be an aqueous, alcoholic solution, or a solution made from more than one solvent. The suitable solvents are but not limited to ethanol, propanol, iso-propanol, DMSO, methanol, ethylene glycol, glycerol, DMF or any solvent that is water immiscible.

The lipid agent can be a micelle or a liposome.

Preparation of said composition is illustrated but not limited to the following example:

Example 9

Liposome Formulation

Ten μl of lipidic polyamine solutions and 10 μl of dioleoylphasphotidyl ethanolamine (DOPE, 50 mg/ml in chloroform, Avanti Polar Lipids, Alabaster, Ala.) were mixed in a glass test tube, the organic solvents were removed by N2 stream followed by vacuum. This formed a thin lipid film deposited on the test tube. One ml of distilled water was added to the test tube and the tube was vortexed to suspend the lipid film to give liposomes. The resulted liposomes are stored at +4° C. till use.

Method of Using

One object of the invention is a method of using said lipopolyamine composition for introducing one or more biologically active agents into cells for the purpose of treating diseases in a vertebrate, generating antibodies to an immunogen in a mammal, or any other suitable purposes. A biologically active agent can be a DNA sequence, a RNA molecule, a synthetic oligonucleotide, a protein with enzymatic activity, a protein or a peptide or the derivative of a protein or a peptide that can bind or inhibit certain molecular interactions, a protein, a peptide, a glycoprotein or a polysaccharide that can stimulate a T-cell or B-cell mediated immune response.

The introduction of a bioactive agent into cells can be done by contacting the lipid agent composition to cells in vitro or in vivo. When the contacting is done in vitro, the formulation is administered to the cells of a vertebrate and the cells are then returned to the vertebrate.

One aspect of this invention relates to the use of the composition for treatment of a disease in a vertebrate wherein the formulation having an effective amount of bioactive agent for treating the disease is administered and the bioactive agent is incorporated into at least one cell of the vertebrate.

The formulation can be applied topically to the skin or mucosal surface; injected into a body cavity; administered orally; injected into a tissue; instilled or inhaled into the airways and alveoli of the vertebrate.

One aspect of this invention relates to the use of the lipid agent formulation to generate antibodies to an immuogen in a mammal. An immunogen can be any protein, peptide, glycoproteins or polysaccharides purified from biological sources, such as inactivated virus or bacteria, or produced by recombinant DNA technology from bacteria, yeast, insect or mammalian cell culture. The lipid agent can serve as an adjuvant to stimulate immune response against the immunogen. The said immunogen can also be a nucleic acid-based sequence that will be produced in transfected cells. The method of use comprises directly administering to mammalian tissue a DNA sequence encoding said immunogen operatively linked to a promoter or a mRNA sequence encoding said immunogen, wherein said sequence is complexed to an amphiphilic polyamine having structure of Formula I in an amount sufficient to induce detectable production of desired antibodies to the expressed immunogen. The administration of the formulation can be accomplished by injection. The injection can be an inoculation through a needle. The mammal tissue can be muscle, skin, or muscous membrane. The mammal can be human or any domestic animals.

The method of using said lipopolyamine composition for introducing a biologically active agent into cell is illustrated in but not limited to the following examples:

Example 10

Transfection and Assay for Reporter Gene Expression

Cos-1 or CV-1 cells are green monkey kidney epithelial cell lines. These cells were routinely maintained under 5% $CO_2$, 100% humidity at 37° C., using DMEM medium supplemented with 10% fetal bovine serum (FBS), L-glutamine and antibiotics. The cells were passed twice per week. The day before transfection, cells were freshly passed in 1 to 3 (Cos-1 cells) or 1 to 4 (CV-1 cells) ratios. For transfection in 96 well plates, pCMVβ-Gal, a plasmid express an *E. Coli* β-galactosidase driven by a CMV promoter was used. The plasmid was amplified in *E. Coli* strain DH-5α, and purified using a Qiagen Maxiprep® kit according to the manufacture's protocol. The resulted DNA was dissolved in distilled water and stored at −20° C. till use.

To prepare liposome DNA complexes, Opti-MEM® medium (Invitrogen) with antibiotics were used to dilute DNA to 4-12 μg/ml, and liposomes to 2-40 μl/ml. Fifty μl of DNA solution and 50 μl of liposome solution were mixed. Meanwhile, cells were treated with trypsin and EDTA and lifted from the plates. An equal volume of culture medium was added to neutralize the action of tryspin. Cells were then centrifuged and the supernatant was removed. Cells were re-suspended in Opti-MEM® supplemented with 10% FBS and antibiotics. About 10,000 to 20,000 cells in 50 μl of medium were added to the DNA-liposome mixture that has been deposited to the multi-well cell culture plate, and the contents were mixed and then returned to the incubator. Cells were harvested by washing once with PBS at the end of 24 hr or 48 hr post transfection to remove dead cells. The cytotoxicity and reporter gene (β-galactosidase) expression were assayed using a dual assay as reported. Cells were lysed in a 50 mM MOPS-NaOH solution, pH 5.0, containing 0.1% Triton X-100, and 10 mM p-nitrophenol phosphate and incubate at room temperature for 20 minutes. After the incubation, the pH was brought back to ~7.8 by adding 5 μl of 0.5 M Tris base. The development of the yellow color was measured at 405 nm to determine the amount of cell-associated acidic phosphate activity, which is roughly proportional to the viable cell number in the tissue culture wells. The enzymatic activity of β-galactosidase was measured after addition of 50 μl of 1 mg/ml chlorophenol red galactopyranose in PBS pH 7.8 containing 1 mM $MgCl_2$ and followed by 5-30 minute incubation at 37° C. OD 570 nm was measured for the product formation.

As positive controls, LipofectAMINE 2000®, Lipofectin® (both are the products from Invitrogen), branched polyethylenimine$_{25,000}$ (Sigma-Aldrich, 200 mM stock solutions in distilled water) were used at various concentrations. The same amount of DNA was used for transfection. A final concentration of 3.3% FBS was included during the transfection as did with other testing formulations.

FIGS. 4*a* and *b* show the transfection efficiency of lipopolyamines-DOPE liposomes. The lipopolyamines were prepared from polyamine and bromoacetamido olean at fixed 1:2 lipid to amine group ratio. It is clear that most of the prepared lipopolyamines showed substantial transfection activity when co-formulated with DOPE at 1:3.5 mole ratios, with two lipopolyamines generated from low generations of dendrimers being considerably more active than those generated from the rest of linear or branched forms of polyamines. The difference in transfection efficiency could be due to one or more than one factors related to the geometric shape of the polyamine group, the charge number, hydrophobic to hydrophilic balance of the molecules, and the difference in cytotoxicity.

FIGS. 5*a-c* show the importance of the co-lipid DOPE in transfection efficiency of three most active lipopolyamines. The pure lipopolyamines by themselves are marginally active. However, their transfection activity is significantly elevated when 2-5 mole ratios cf DOPE is included. In the presence of DOPE, the lipid suspension is significantly more turbid than the pure compound, suggesting that they exist as liposomes. The presence of DOPE also enhanced the transfection efficiency when liposomes to DNA ratio were relatively low. It was estimated that the amount of cationic charges of the liposomes, (assuming 100% protonated), under the peak transfection condition, is close to or even less than the total negative charges contributed from the DNA molecules. For example, for PAMAM-G0-AOA4, 0.5 μl of liposomes contain 0.1 nmole of lipopolyamine or about 0.6 nmoles of cationic charges when it is fully protonated, while 0.3 μg of DNA contains 0.9 nmoles of negative charges based on the fact that 1 μg DNA contains roughly 3 nmoles of negative charges due to phosphate groups (the average MW for nucleic acid monomer is ~330). Not all the weak amino groups in the lipopolyamines are expected to be fully protonated and become charged under the physiological pH. This suggests that the lipopolyamine-DOPE combination possesses some very unique biological activities that none other cationic liposome or polymer systems has. So far, all the existing systems require an excessive cationic to anionic charge ratio for the optimal transfection activities (Eppstein, et al., (1990) U.S. Pat. No. 4,897,355; Epand, et al, (1994) U.S. Pat. No. 5,283,185; Behr et al (1989) Proc. Natl. Acad. Sci. USA, 86, 6982-6, and Yamazaki et al (2000) Gene Therapy 7, 1148-1155). The ability of lipopolyamine-DOPE liposomes mediating efficient transfection at low cationic to anionic charge ratio would explain the relatively low toxicity of these liposomes to cells at the optimal transfection dosages, as they are less charged and thus bind less to cells. In fact, higher liposome-to-DNA ratios hamper the transfection activity and this is accompanied with an increased toxicity. This can be explained as increased cell uptake as the charge ratio of liposome-DNA complexes is approaching net positive. The high transfection efficiency at a net anionic charge ratio would also explain the relatively low sensitivity for these liposomes towards serum, as most likely the anionic proteins and lipids present in the serum are the causes that reduce the transfection efficiency of the cationic liposome-DNA complexes, as these proteins are capable of binding and coating the complexes and reduce the cell uptake of these complexes. Such an event is less likely to occur due to the net anionic surface charges on the complexes for these lipopolyamine-DOPE:DNA complexes.

FIG. 6 shows that the optimal DNA dosages for an efficient transfection using lipopolyamine DAB-Amb-AOA6:DOPE (1:3.5) requires a minimal of 0.2 μg/well for 96 well plates, while the optimal dosages appeared to be ≥0.3 μg/well. Once again, the optimal transfection occurs at a net negative charge ratios, as the increased DNA dosages had little effect on the transfection efficiency.

FIG. 7 shows the transfection efficiency of several well known and widely used commercial transfection reagents. The experiment was performed simultaneously as those presented in FIGS. 5 and 6. Both PAMAM G0-AOA4 and DAB-Am8-AOA6 co-formulated with DOPE compared very favorably to the commercial products, LipofectAMINE 2000®, Lipofectin® or PEI25,000. We therefore concluded that lipopolyamines prepared from low generations of dendritic polyamines, carrying multiple long chain lipids and co-formulated with DOPE are unique transfection reagents that can mediate efficient transfection at low lipid to DNA ratios, less sensitive to interfering components in the serum and mild to cells when used at optimal dosages. These features allow a simplified and rapid transfection protocol which does not require the removal of serum during transfection and the DNA-liposome complexes after the transfection that resulted in considerable savings on time involved in transfection experiments.

The following documents can be used as needed to practice various claimed embodiments: U.S. Pat. No. 4,897,355, Eppstein, et al; U.S. Pat. No. 5,283,185, Epand, et al; U.S. Pat. No. 5,393,797, Hedstrand and Tomalia; U.S. Pat. No. 5,650,096, Harris, et al; U.S. Pat. No. 6,716,882, Haces, et al; and U.S. Pat. No. 7,067,697, Gao. Other publications: Behr, et al (1989) *Proc Natl Acad Sci USA* 86:6982-6; Boussif, et al (1989) *Proc Natl Acad Sci USA* 1995 92:7297-301; Chen, et al, (2000) *Biomacromolecules* 1: 471-80; Kramer, et al (2002) *Angew Chem Int ed* 41:4252-6; Mizutani, et al (2002) *J Colloid Interface Sci* 248: 493-8; Murugan, et al (2004) *Langmuir* 20: 8307-12; Schenning, et al, (1998) *J Am Chem Soc* 120: 8199-208; Sui, et al, (2003) *J Colloid Interface Sci* 250: 364-70; Yamazaki, et al (2000) *Gene Therapy* 7: 1148-1155, and EP 1,133,465 B1 to Gao et al. (2004).

All references cited herein are hereby incorporated by reference in their entirety.

Additional Embodiment

Bromoacetyl lipid-derivative can also be conjugated to the polyamines at room temperature, for example 20° C. to 35° C., at a ratio of lipid to polyamine of 1:1 to 6:1 in methanol for example. Reaction can be completed after 48 hours for example. No additional base is needed.

Additional Embodiments

In one embodiment, there is provided a lipopolyamine comprising:

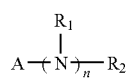

Formula I wherein
A$-(N)_n$ is linear, branched or dendritic polyamine, wherein n=3-100;
$R_1$ is independently H, or a substitute of structure (X—Y—Z) wherein
X=$(CH_2)_i$, wherein i=0-12 and when i=0, X is a bond, —$(CH_2)_iC(O)$—, —$(CH_2)_iNH$— wherein i=0-12, or —$CH_2CH(OH)CH_2$—,
Y=a bond, —C(O)NH—, NHC(O), —$CH_2$—, —O—, —C(O)O—, or —C(O)—;
Z=linear or branched alkyl or alkenyl chain having 4-40 carbon units;
$R_2$ is a substitute of structure of $(X—Y—Z)_m$, wherein
X=—$(CH_2)_i$—, wherein i=0-12 and when i=0, X is a bond, —$(CH_2)_iC(O)$—, —$(CH_2)_iNH$— wherein i=0-12, or —$CH_2CH(OH)CH_2$—,
Y=a bond, —C(O)NH—, —NHC(O)—, —$CH_2$—, —O—, —C(O)O—, or —C(O)—;
Z=linear or branched alkyl or alkenyl chain having 4-40 carbon units;
m is at least 1 or any integer between 1 to 2n;
in pure form or in mixture of isomers, or in form of any lipid polymorphism phase known to exist, or its solvates, hydrates, isomers, and any salts, for example pharmaceutically acceptable salts.

In one embodiment, A$-(N)_n$ is spermidine (SPMD), spermine (SPM), tris-(2-aminoethyl)amine (TEA), pentaethylenehexamine (PEHA), branched polyethylenimine (PEI), PAMAM dendrimer G0, PAMAM dendrimer G1, DAB-Am4 dendrimer, DAB-Am8 dendrimer, DAB-Am 16 dendrimer, or polyethylenimine MW about 800.

In one embodiment, A$-(N)_n$ is spermidine, X is —$CH_2$—, Y is —C(O)NH—, Z is oleyl, and m is at least 1 or any integer between 1 to 2n.

In one embodiment, A$-(N)_n$ is spermine, X is —$CH_2$—Y is —C(O)NH—, Z is oleyl, and m is at least 1 or any integer between 1 to 2n.

In one embodiment, A$-(N)_n$ is tris-(2-aminoethyl)amine, X is —$CH_2$—, Y is —C(O)NH—, Z is oleyl, and m is at least 1 or any integer between 1 to 2n.

In one embodiment, A$-(N)_n$ is PEHA, X is —$CH_2$—, Y is —C(O)NH—, Z is oleyl, and m is at least 1 or any integer between 1 to 2n.

In one embodiment, A$-(N)_n$ is a branched PEI, X is —$CH_2$—, Y is —C(O)NH—, Z is oleyl, and m is at least 1 or any integer between 1 to 2n.

In one embodiment, A$-(N)_n$ is PAMAM dendrimer G0, X is —$CH_2$—, Y is —C(O)NH—, Z is oleyl, and m is at least 1 or any integer between 1 to 2n.

In one embodiment, A$-(N)_n$ is PAMAM dendrimer G1, X is —$CH_2$—, Y is —C(O)NH—, Z is oleyl, and m is at least 1 or any integer between 1 to 2n.

In one embodiment, A$-(N)_n$ is DAB-Am4 dendrimer, X is —$CH_2$—, Y is —C(O)NH—, Z is oleyl, and m is at least 1 or any integer between 1 to 2n.

In one embodiment, A$-(N)_n$ is DAB-Am8 dendrimer, X is —$CH_2$—, Y is —C(O)NH—, Z is oleyl, and m is at least 1 or any integer between 1 to 2n.

In one embodiment, A$-(N)_n$ is DAB-Am16 dendrimer, X is —$CH_2$—, Y is —C(O)NH—, Z is oleyl, and m is at least 1 or any integer between 1 to 2n.

In one embodiment, A$-(N)_n$ is DAB-Am8 dendrimer, X is —$CH_2CH(OH)CH_2$—, Y is —O—, Z is oleyl, and m is at least 1 or any integer between 1 to 2n.

In one embodiment, A$-(N)_n$ is DAB-Am8 dendrimer, X is a bond, Y is a bond, Z is oleyl, and m is at least 1 or any integer between 1 to 2n.

In one embodiment, X is —$(CH_2)_iC(O)$— wherein i=0-12.
In one embodiment, X is —$(CH_2)_iNH$— wherein i=0-12.
In one embodiment, X is —$(CH_2)_i$—, wherein i=0-12.
In one embodiment, X is —$CH_2CHOHCH_2$—.
In one embodiment, Y is —C(O)NH—.
In one embodiment, Y is —NHC(O)—.
In one embodiment, Z is (Z)-octadec-9-enyl (oleyl).

In one embodiment, there is provided a composition which is useful for introducing a biologically active agent into cell, comprising
a lipid agent comprising an aforementioned lipopolyamine;
one or more biologically active agents; and
one or more pharmaceutically acceptable solvents, carriers, and/or additives.

In one embodiment, the composition is a liposome formulation.

In one embodiment, the composition is an emulsion

In one embodiment, the composition is a micelle formulation

In one embodiment, said biologically active agent is a polynucleotide, polypeptide, or a drug.

In one embodiment, the composition further comprises one or more helper lipids.

In one embodiment, said polynucleotide is DNA or mRNA coding for a polypeptide which is expressed after said DNA or mRNA is taken up into a cell.

In one embodiment, said polynucleotide is DNA or RNA.

In one embodiment, said nucleotide is an oligonucleotide in single stranded form, or in fully or partially complementary double stranded form.

In one embodiment, said oligonucleotide has diester linkage or other chemically modified linkage.

In one embodiment, the helper lipids is cholesterol or its derivatives, monoacyl or diacyl phosphatidyl choline, monoacyl or diacyl phosphatidyl ethanolamine, monoacyl or diacyl phosphatidyl serine, dioleolphasphotidyl ethanolamine (DOPE), or single chain fatty alcohol, fatty acid or fatty amine.

In one embodiment, the helper lipid is DOPE.

In one embodiment, $A-(N)_n$ is SPMD, X is $-CH_2-$, Y is $-C(O)NH-$, Z is oleyl, m is at least 1 or any integer between 1 to 2n, and said bioactive agent is DNA.

In one embodiment, $A-(N)_n$ is SPM, X is $-CH_2-$, Y is $-C(O)NH-$, Z is oleyl, m is at least 1 or any integer between 1 to 2n, and said bioactive agent is DNA.

In one embodiment, $A-(N)_n$ is TEA, X is $-CH_2-$, Y is $-C(O)NH-$, Z is oleyl, m is at least 1 or any integer between 1 to 2n, and said bioactive agent is DNA.

In one embodiment, $A-(N)_n$ is PEHA, X is $-CH_2-$, Y is $-C(O)NH-$, Z is oleyl, m is at least 1 or any integer between 1 to 2n, and said bioactive agent is DNA.

In one embodiment, $A-(N)_n$ is branched PEI, X is $-CH_2-$, Y is $-C(O)NH-$, Z is oleyl, m is at least 1 or any integer between 1 to 2n, and said bioactive agent is DNA.

In one embodiment, $A-(N)_n$ is PAMAM dendrimer G0, X is $-CH_2-$ Y is $-C(O)NH-$, Z is oleyl, m is at least 1 or any integer between 1 to 2n, and said bioactive agent is DNA.

In one embodiment, $A-(N)_n$ is PAMAM dendrimer, G1, X is $-CH_2-$, Y is $-C(O)NH-$, Z is oleyl, m is at least 1 or any integer between 1 to 2n, and said bioactive agent is DNA.

In one embodiment, $A-(N)_n$ is DAB-Am4 dendrimer, X is $-CH_2-$, Y is $-C(O)NH-$, Z is oleyl, m is at least 1 or any integer between 1 to 2n, and said bioactive agent is DNA.

In one embodiment, $A-(N)_n$ is DAB-Am8 dendrimer, X is $-CH_2-$, Y is $-C(O)NH-$, Z is oleyl, m is at least 1 or any integer between 1 to 2n, and said bioactive agent is DNA.

In one embodiment, $A-(N)_n$ is DAB-Am16 dendrimer, X is $-CH_2-$, Y is $-C(O)NH-$, Z is oleyl, m is at least 1 or any integer between 1 to 2n, and said bioactive agent is DNA.

In one embodiment, $A-(N)_n$ is DAB-Am8 dendrimer, X is $-CH_2CH(OH)CH_2-$, Y is $-O-$, Z is oleyl, m is at least 1 or any integer between 1 to 2n, and said bioactive agent is DNA.

In one embodiment, $A-(N)_n$ is DAB-Am8 dendrimer, X is a bond, Y is a bond, Z is oleyl, m is at least 1 or any integer between 1 to 2n, and said bioactive agent is DNA.

In one embodiment, there is provided a process of preparing an aforementioned lipopolyamine, comprising a step of covalently coupling a polyamine with a reactive lipid or lipid intermediate.

In one embodiment, the polyamine is spermidine (SPMD), spermine (SPM), tris-(2-aminoethyl)amine (TEA), pentaethylenehexamine(PEHA), linear polyethylenimine (LPEI) PAMAM dendrimer G0, PAMAM dendrimer G1, DAB-Am4 dendrimer, DAB-Am8 dendrimer, DAB-Am 16 dendrimer, or polyethylenimine of MW 800.

In one embodiment, the lipid is fatty amine, fatty alcohol, fatty acid, or saturated or unsaturated fatty hydrocarbon.

In one embodiment, the lipid intermediate is haloacetamido lipid, lipid haloethylamide, epoxy ether lipid, acryloylamido lipid, or lipid halide.

In one embodiment, the lipid intermediate is 2-bromoacetamido-olean, 2-chloroacetamido-olean, N-oleoyl-2-bromoethylamide, N-oleoyl-2-chloroethylamide, 2-acryloylamido-olean, oleyl glycidyl ether, or oleyl bromide.

In one embodiment, there is provided a method of using an aforementioned composition comprising administration of said composition in vitro or in vivo.

In one embodiment, there is provided a method of treating a disease in a vertebrate, comprising administration of an effective amount of an aforementioned composition to at least one cell from said vertebrate and allowing the bioactive agent incorporated into said cell(s); and returning said cell(s) to said vertebrate.

In one embodiment, there is provided a method of treatment of a disease in a vertebrate, comprising administration of an effective amount of an aforementioned composition, wherein said composition is applied topically to the skin or mucosal surface, injected into a body cavity, administered orally, injected into a tissue, or instilled or inhaled into the airways and alveoli of said vertebrate.

In one embodiment, there is provided a method of generating antibodies to an immunogen in a mammal, comprising directly administering to said mammalian tissue an effective amount of an aforementioned composition wherein said bioactive agent is a DNA sequence encoding said immunogen operatively linked to a promoter or a mRNA sequence encoding said immunogen, wherein said sequence is in an amount sufficient to induce detectable production of desired antibodies to the expressed immunogen.

In one embodiment, the tissue is muscle, skin, or mucous membrane.

In one embodiment, the administration is accomplished by injection.

In one embodiment, there is provided a method of generating antibodies to an immunogen in a mammal, comprising directly administering to said mammalian tissue an effective amount of an aforementioned composition wherein said bioactive agent is a purified or partially purified protein, a synthetic peptide, a glycoprotein, or a polysaccharide.

In one embodiment, there is provided a composition which is useful for introducing one or more biologically active agents into cell, comprising
a lipid agent comprising a hydrophilic core of polyamine and a lipophilic shell of lipid tail,
one or more bioactive agents embedded in said lipid agent,
a second helper lipid, and
one of more pharmaceutically acceptable solvents, carriers, and/or additives.

In one embodiment, said lipid agent is a liposome of lipopolyamines, wherein the amino groups on said polyamine are connected to said lipid tail through a covalent bond with or without a spacer X, and bond Y.

In one embodiment, said lipopolyamine is formed by reacting SPMD, SPM, TEA, PEHA, branched PEI, PAMAM G0, PAMAM G1, DAB-Am 4, DAB-Am 8, or DAB-Am 16, with bromoacetamido olean.

In one embodiment, said lipopolyamine is formed by reacting SPMD, SPM, TEA, PEHA, branched PEI, PAMAM G0, PAMAM G1, DAB-Am 4, DAB-Am 8, or DAB-Am 16 with oleyl glycidyl ether.

In one embodiment, said polyamine is SPM, TEA, PEHA, branched PEI, PAMAM G0, PAMAM G1, DAB-Am 4, DAB-Am 8, or DAB-Am 16, spacer X is a —$CH_2$— group, said bond Y is —C(O)NH—.

In one embodiment, said polyamine is SPM, TEA, PEHA, branched PEI, PAMAM G0, PAMAM G1, DAB-Am 4, DAB-Am 8, or DAB-Am 16, spacer X is —$CH_2$C(O)$CH_2$— and Y is —O—.

In one embodiment, said bioactive agent is polynucleotide, polypeptide, glycoprotein, polysaccharide, or chemical drug.

In one embodiment, said polynucleotide is DNA or RNA.

In one embodiment, said bioactive agent is polynucleotide, polypeptide, glycoprotein, polysaccharide, or chemical drug.

In one embodiment, said polynucleotide is DNA or RNA.

In one embodiment, the helper lipid is cholestrol or its derivatives, monoacyl or diacyl phosphatidyl choline, mono or diacyl phosphatidyl ethanolamine, monoacyl or diacyl phophatidyl serine, DOPE, or single chain fatty alcohol, fatty acid or fatty amine.

In one embodiment, the helper lipid is DOPE.

In one embodiment, there is provided a composition useful for introducing one or more biologically active agents into cell, comprising
  a lipid agent comprising oleyl modified SPMD, wherein said oleyl is connected to said SPMD through an acetamido bond,
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified SPM, wherein said oleyl is connected to said SPM through an acetamido bond,
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified TEA, wherein said oleyl is connected to said TEA through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified PEHA, wherein said oleyl is connected to said PEHA through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified branched PEI, wherein said oleyl is connected to said branched PEI through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified PAMAM G0, wherein said oleyl is connected to said PAMAM G0 through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified PAMAM G1, wherein said oleyl is connected to said PAMAM G1 through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified DAB-Am4, wherein said oleyl is connected to said DAB-Am4 through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified DAB-Am8, wherein said oleyl is connected to said DAB-Am8 through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified DAB-Am16, wherein said oleyl is connected to said DAB-Am8 through an acetamido bond.
  a DNA or RNA embedded in said lipid agent,
  a helper lipid DOPE, and
  one of more pharmaceutically acceptable solvents, carriers, and/or additives.

In one embodiment, there is provided a composition useful for introducing one or more biologically active agents into cell, comprising
  a lipid agent comprising oleyl modified DAB-Am8, wherein said oleyl is connected to said DAB-Am8 through a —O$CH_2$CHOHCH$_2$— spacer
  a DNA or RNA embedded in said lipid agent,
  a helper lipid DOPE, and one of more pharmaceutically acceptable solvents, carriers, and/or additives.

In one embodiment, there is provided a composition useful for introducing one or more biologically active agents into cell, comprising
  a lipid agent comprising oleyl modified DAB-Am8, wherein said oleyl is directly connected to said DAB-Am8
  a DNA or RNA embedded in said lipid agent,
  a helper lipid DOPE, and
  one or more pharmaceutically acceptable solvents, carriers, and/or additives.

In one embodiment, there is provided a method of using an aforementioned composition, comprising administration of an effective amount of the composition in vitro or in vivo.

In one embodiment, there is provided a method of treating a disease in a vertebrate, comprising administration of an effective amount of an aforementioned composition to at least one cell from said vertebrate and allowing the bioactive agent incorporated into said cell(s); and returning said cell(s) to said vertebrate.

In one embodiment, there is provided a method of treatment of a disease in a vertebrate, comprising administration of an effective amount of an aforementioned composition, wherein said composition is applied topically to the skin or mucosal surface, injected into a body cavity, administered orally, injected into a tissue, or instilled or inhaled into the airways and alveoli of said vertebrate.

In one embodiment, there is provided a method of generating antibodies to an immunogen in a mammal, comprising directly administering to said mammalian tissue an an effective amount of aforementioned composition wherein said bioactive agent is a DNA sequence encoding said immunogen operatively linked to a promoter or a mRNA sequence encoding said immunogen, wherein said sequence is in an amount sufficient to induce detectable production of desired antibodies to the expressed immunogen.

In one embodiment, the tissue is muscle, skin, or mucous membrane.

In one embodiment, there is provided a the administration is accomplished by injection.

In one embodiment, there is provided a method of generating antibodies to an immunogen in a mammal, comprising directly administering to said mammalian tissue an effective amount of an aforementioned composition wherein said bioactive agent is a purified or partially purified protein, a synthetic peptide, a glycoprotein, or a polysaccharide.

In one embodiment, there is provided a composition comprising:
  an aqueous media,
  micelles dispersed in the aqueous media,
  wherein the micelles comprise:
    at least one polyamine, and at least one lipid covalently bonded to the polyamine,
    wherein the polyamine comprises about 3 to about 500 nitrogen atoms.

In some embodiments, the spermidine (SPMD), spermine (SPM), tris-(2-aminoethyl)amine (TEA), pentaethylenehexamine (PEHA), branched polyethylenimine (PEI), PAMAM dendrimer G0, PAMAM dendrimer G1, DAB-Am4 dendrimer, DAB-Am8 dendrimer, or DAB-Am16 dendrimer are modified by oleylamine through acetamido bond, or they can be modified by oleyl alcohol through —CH$_2$CHOHCH$_2$— group.

In some embodiments, the lipid agent comprises a hydrophilic shell of polyamine and a lipophilic core of lipid tail.

More Additional Embodiments

In one embodiment, there is provided a lipopolyamine comprising:

Formula I

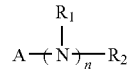

Wherein
A—(N)$_n$ is linear, branched or dendritic polyamine, wherein n=3-100;
R$_1$ is independently H, or a substitute of structure (X—Y—Z) wherein
  X=—(CH$_2$)$_i$—, wherein i=0-12 and when i=0, X is a bond, —(CH$_2$)$_i$C(O)—, —(CH$_2$)$_i$NH— wherein i=0-12, or —CH$_2$CH(OH)CH$_2$—;
  Y=a bond, —C(O)NH—, —NHC(O)—, —CH$_2$—, —O—, —C(O)O— or —C(O)—;
  Z=linear or branched alkyl chain or alkenyl chain having 4-40 carbon units;
  wherein the chain has zero to six double bond;
R$_2$ is a substitute of structure of (X—Y—Z)$_m$, wherein
  X=—(CH$_2$)$_i$— wherein i=0-12 and when i=0, X is a bond, —(CH$_2$)$_i$C(O)—, —(CH$_2$)$_i$NH— wherein i=0-12, or —CH$_2$CH(OH)CH$_2$—;
  Y=a bond, —C(O)NH—, —NHC(O)—, —CH$_2$—, —O—, —C(O)O— or —C(O)—;
  Z=linear or branched alkyl chain or alkenyl chain having 4-40 carbon units;
  wherein the chain has zero to six double bond;
  m is at least 1 or any integer between 1 to 2n;
in pure form or in mixture of isomers, or in form of any lipid polymorphism phase known to exist, or its solvates, hydrates, isomers, and any salts, for example pharmaceutically acceptable salts.

In one embodiment, A—(N)$_n$ is spermidine (SPMD), spermine (SPM), tris-(2-aminoethyl)amine (TEA), pentaethylenehexamine (PEHA), branched polyethylenimine (PEI), PAMAM dendrimer G0, PAMAM dendrimer G1, DAB-Am4 dendrimer, DAB-Am8 dendrimer, or DAB-Am 16 dendrimer; X is —CH$_2$—, Y is —C(O)NH—, Z is oleyl, and m is at least 1 or any integer between 1 to 2n.

In one embodiment, A—(N)$_n$ is DAB-Am8 dendrimer, X is —CH$_2$CH(OH)CH$_2$—, Y is —O—, Z is oleyl, and m is at least 1 or any integer between 1 to 2n.

In one embodiment, A—(N)$_n$ is DAB-Am8 dendrimer, X is a bond, Y is a bond, Z is oleyl, and m is at least 1 or any integer between 1 to 2n.

In one embodiment, there is provided a composition which is useful for introducing a biologically active agent into cell, comprising
  a lipid agent comprising an aforementioned lipopolyamine;
  one or more biologically active agents; and
  one or more pharmaceutically acceptable solvents, carriers, and/or additives.

In one embodiment, the composition is a liposome formulation or a micelle formulation.

In one embodiment, said biologically active agent is a polynucleotide, polypeptide, protein, glycoprotein, polysaccharide, or a small molecular weight drug.

In one embodiment, said polynucleotide is DNA or mRNA coding for a polypeptide, an antisense RNA, or a microRNA, which is expressed after said DNA or mRNA is taken up into a cell.

In one embodiment, said polynucleotide is an oligonucleotide of up to 200 nucleotides in length, in single stranded form, or in fully or partially complementary double stranded form.

In one embodiment, said polynucleotide is siRNA (small interfering RNA).

In one embodiment, the composition further comprises one or more helper lipids selected from the group consisting of cholesterol or its derivatives, monoacyl or diacyl phosphatidyl choline, monoacyl or diacyl phosphatidyl ethanolamine, monoacyl or diacyl phosphatidyl serine, dioleolphasphotidyl ethanolamine (DOPE), single chain fatty alcohol, single chain fatty acid, and single chain fatty amine.

In one embodiment, there is provided a composition which is useful for introducing one or more biologically active agents into cell, comprising
a lipid agent comprising a hydrophilic shell of polyamine and a lipophilic core of lipid tail, wherein the amino group of the polyamine are connected to the lipid tail through a covalent bond with or without a spacer,
one or more bioactive agents embedded in said lipid agent, and
one of more pharmaceutically acceptable solvents, carriers, and/or additives.

In some embodiments, the lipid is a C4 to C40 carbon chain having zero to six double bond. In some embodiments, the lipid agent comprises a hydrophilic core of polyamine and a lipophilic shell of lipid tail.

In one embodiment, the composition further comprises
a second helper lipid selected from the group consisting choplestrol or its derivatives, monoacyl or diacyl phosphatidyl choline, mono or diacyl phosphatidyl ethanolamine, monoacyl or diacyl phophatidyl serine, DOPE, or single chain fatty alcohol, fatty acid or fatty amine.

In one embodiment, the bioactive agent is polynucleotide, polypeptide, glycoprotein, protein, polysaccharide, or small molecular weight drug.

In one embodiment, the polynucleotide is DNA or mRNA coding for a polypeptide which is expressed after said DNA or mRNA is taken up into a cell.

In one embodiment, the polynucleotide is an oligonucleotide in single stranded form, or in fully or partially complementary double stranded form.

In one embodiment, the polynucleotide is siRNA (small interfering RNA).

In one embodiment, there is provided a composition comprising
the lipid agent comprising oleyl modified SPMD, oleyl modified SPM, oleyl modified TEA, oleyl modified PEHA, or oleyl modified branched PEI, oleyl modified PAMAM G0, oleyl modified PAMAM G1, or oleyl modified DAB-Am4, oleyl modified DAB-Am8, or oleyl modified DAB-Am 16, wherein said oleyl chain is connected to said SPMD, SPM, TEA, PEHA, branched PEI, PAMAM G0, PAMAM G1, DAB-Am8, or DAB-Am16 respectively, through an acetamido bond,
a bioactive agent which is DNA or RNA embedded in said lipid agent, and
a helper lipid which is DOPE.

In one embodiment, there is provided a composition comprising
a lipid agent comprises oleyl modified DAB-Am8, wherein said oleyl chain is connected to said DAB-Am8 through a O—CH$_2$CHOHCH$_2$— spacer.
a bioactive agent which is a DNA or RNA embedded in said lipid agent, and
a helper lipid which is DOPE.

In one embodiment, there is provided a composition comprising
a lipid agent comprising oleyl modified DAB-Am8, wherein said oleyl is directly connected to said DAB-Am8,
a bioactive agent which is a DNA or RNA embedded in said lipid agent, and
a helper lipid which is DOPE.

In one embodiment, there is provided a method for introducing one or more biologically active agents into cell, comprising introducing an aforementioned composition into a cell.

In one embodiment, there is provided a method for introducing one or more biologically active agents into cell, comprising
introducing a composition into a cell,
wherein the composition comprising oleyl modified SPMD, or oleyl modified SPM, oleyl modified TEA, or oleyl modified PEHA, or oleyl modified branched PEI, oleyl modified PAMAM G0, or oleyl modified PAMAM G1, or oleyl modified DAB-Am4, or oleyl modified DAB-Am8, or oleyl modified DAB-Am16,
a bioactive agent selected from polynucleotide, polypeptide, glycoprotein, protein, polysaccharide, or small molecular weight drug,
a helper lipid selected from cholestrol or its derivatives, monoacyl or diacyl phosphatidyl choline, mono or diacyl phosphatidyl ethanolamine, monoacyl or diacyl phophatidyl serine, DOPE, or single chain fatty alcohol, fatty acid or fatty amine; and
one of more pharmaceutically acceptable solvents, carriers, and/or additives, wherein the composition is a liposome, an emulsion or a micelle formulation.

In some embodiments, small molecular weight drugs are drugs having molecular weight lower than 3000 Da for example.

The invention claimed is:
1. A composition which is useful for introducing a biologically active agent into a cell as a transfection agent, comprising:
a lipopolyamine comprising:

Formula I

Wherein
A—(N)$_n$ is linear, branched or dendritic polyamine, wherein n=3-100, wherein n is the number of amino groups in the polyamine;
R$_1$ is independently H, or a substitute of structure (X—Y—Z) wherein
X=(CH$_2$)$_i$, wherein i=1-12;
Y=—C(O)NH—, —NHC(O)—, —CH$_2$—, —O—, —C(O)O—, or —C(O)—;
Z=linear or branched alkyl chain or alkenyl chain having 4-40 carbon atoms in length;
wherein the chain has zero to six double bonds;
R$_2$ is a substitute of structure of (X—Y—Z)$_m$, wherein
X=—(CH$_2$)$_i$—, wherein i=1-12,
Y=—C(O)NH—, —NHC(O)—, —CH$_2$—, —O—, —C(O)O—, or —C(O)—;
Z=linear or branched alkyl chain or alkenyl chain having 4-40 carbon atoms in length;

wherein the chain has zero to six double bonds;
m is at least 1;
and wherein the lipopolyamine is mixed with one or more helper lipids which elevates transfection activity;
and further comprising one or more biologically active agents; and one or more pharmaceutically acceptable solvents, carriers and/or additives;
and wherein the composition is an aqueous liposome formulation.

2. The composition according to claim 1, wherein A$-$(N)$_n$ is spermidine (SPMD), spermine (SPM), tris-(2-aminoethyl)amine (TEA), pentaethylenehexamine (PEHA), branched polyethylenimine (PEI), PAMAM dendrimer G0, PAMAM dendrimer G1, DAB-Am4 dendrimer, DAB-Am8 dendrimer, or DAB-Am 16 dendrimer; X is —CH$_2$—, Y is —C(O)NH—, Z is oleyl, and m is at least 1.

3. The composition according to claim 1, wherein A$-$(N)$_n$ is DAB-Am8 dendrimer, X is —CH$_2$CH(OH)CH$_2$—, Y is —O—, Z is oleyl, and m is at least 1.

4. The composition according to claim 1, wherein said biologically active agent is a polynucleotide, polypeptide, protein, glycoprotein, polysaccharide, or any anionic small molecular weight drug.

5. The composition according to claim 4, wherein said polynucleotide is a DNA that can be transcribed into a mRNA that codes for a polypeptide, an antisense RNA for a primary transcripted mRNA, or a microRNA which is expressed after said DNA is taken up into a cell.

6. The composition according to claim 4, said polynucleotide is an oligonucleotide composed of up to 200 nucleotides in length, in single stranded form, or in fully or partially complementary double stranded form.

7. The composition according to claim 4, wherein said polynucleotide is siRNA (small interfering RNA) or a microRNA.

8. The composition according to claim 1, wherein the one or more helper lipids is selected from the group consisting of cholesterol or its derivatives, monoacyl or diacyl phosphatidyl choline, monoacyl or diacyl phosphatidyl ethanolamine, monoacyl or diacyl phosphatidyl serine, dioleolphasphotidyl ethanolamine (DOPE), single chain fatty alcohol, single chain fatty acid, and single chain fatty amine.

9. The composition according to claim 1, wherein the helper lipid is DOPE.

10. A composition which is useful for introducing a biologically active agent into a cell as a transfection agent, comprising: a lipopolyamine comprising:

Formula I wherein
A$-$(N)$_n$ is linear, branched or dendritic polyamine, wherein n=3-100 wherein n is the number of amino groups in the polyamine;
R$_1$ is independently H, or a substitute of structure (X—Y—Z) wherein
X=(CH$_2$)$_i$, wherein i=1-12;
Y=—C(O)NH—, —NHC(O)—, —CH$_2$—, —O—, —C(O)O—, or —C(O)—;
Z=linear or branched alkyl chain or alkenyl chain having 4-40 carbon atoms in length;
wherein the chain has zero to six double bonds;
R$_2$ is a substitute of structure of (X—Y—Z)$_m$, wherein
X=—(CH$_2$)$_i$—, wherein i=1-12,
Y=—C(O)NH—, —NHC(O)—, —CH$_2$—, —O—, —C(O)O—, or —C(O)—;
Z=linear or branched alkyl chain or alkenyl chain having 4-40 carbon atoms in length;
wherein the chain has zero to six double bonds;
m is at least 1;
and wherein the lipopolyamine is mixed with one or more helper lipids which elevates transfection activity;
and further comprising one or more biologically active agents; and one or more pharmaceutically acceptable solvents, carriers and/or additives;
and wherein the composition is an aqueous liposome.

11. The composition according to claim 10, wherein A$-$(N)$_n$ is spermidine (SPMD), spermine (SPM), tris-(2-aminoethyl)amine (TEA), pentaethylenehexamine (PEHA), branched polyethylenimine (PEI), PAMAM dendrimer G0, PAMAM dendrimer G1, DAB-Am4 dendrimer, DAB-Am8 dendrimer, or DAB-Am 16 dendrimer; X is —CH$_2$—, Y is —C(O)NH—, Z is oleyl, and m is any integer between 1 to 2n.

12. The composition according to claim 10, wherein A$-$(N)$_n$ is DAB-Am8 dendrimer, X is —CH$_2$CH(OH)CH$_2$—, Y is —O—, Z is oleyl, and m is any integer between 1 to 2n.

* * * * *